United States Patent [19]

Kreutzberger et al.

[11] Patent Number: 4,762,833
[45] Date of Patent: Aug. 9, 1988

[54] 2,4,6-TRIS-TERTIARY-BUTYLAMINO-1,3,5-TRIAZINE USEFUL FOR THE PROPHYLAXIS AND TREATMENT OF EPILEPSY AND ANXIETY STATES

[75] Inventors: Alfred Kreutzberger, Mainz; Alfons Söder, Frankfurt am Main; Hermann J. Gerhards, Hofheim am Taunus, all of Fed. Rep. of Germany

[73] Assignee: Hoechst Aktiengesellschaft, Frankfurt, Fed. Rep. of Germany

[21] Appl. No.: 33,628

[22] Filed: Apr. 3, 1987

[30] Foreign Application Priority Data

Apr. 5, 1986 [DE] Fed. Rep. of Germany ....... 3611425

[51] Int. Cl.$^4$ ..................... A61K 31/53; C07D 251/54
[52] U.S. Cl. ..................... 514/245; 544/196
[58] Field of Search ........................ 544/196; 514/245

[56] References Cited

U.S. PATENT DOCUMENTS 2,691,021 10/1954 Kaiser et al. ..................... 544/196
3,591,693 7/1971 Cantrall et al. ..................... 514/245
3,706,741 12/1972 Papaioannou ..................... 544/196
4,269,832 5/1981 Tomcufcik et al. ................ 514/183

OTHER PUBLICATIONS

Kadota et al., Chemical Abstracts, vol. 88 (13): 89718c, Mar. 27, 1978, p. 527.

Primary Examiner—Mary C. Lee
Assistant Examiner—Zinna Northington
Attorney, Agent, or Firm—Finnegan, Henderson, Farabow, Garrett & Dunner

[57] ABSTRACT

2,4,6-Tris-tertiary-butylamino-1,3,5-triazine of the formula I

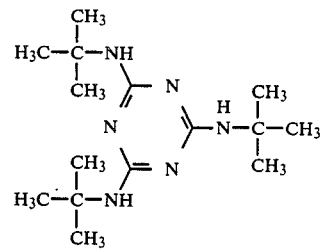

for the prophylaxis and treatment of epilepsy and anxiety states, and the use for the preparation of a medicament for the prophylaxis and treatment of epilepsy and anxiety states, are described.

2 Claims, No Drawings

2,4,6-TRIS-TERTIARY-BUTYLAMINO-1,3,5-TRIAZINE USEFUL FOR THE PROPHYLAXIS AND TREATMENT OF EPILEPSY AND ANXIETY STATES

The invention relates to 2,4,6-tris-tertiary-butylamino-1,3,5-triazine of the formula I

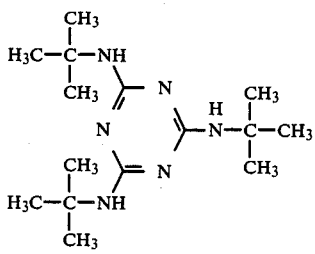

for the prophylaxis and treatment of epilepsy and anxiety states.

2,4,6-Tris-tertiary-butylamino-1,3,5-triazine has already been described (cf. for example U.S. Pat. No. 2,691,021). According to the statements in the literature this 1,3,5triazine derivative is used for the preparation of synthetic resins and surface-active substances (U.S. Pat. No. 2,691,021). The use to counter mycobacteria (U.S. Pat. No. 3,591,693 and U.S. Pat. No. 3,706,741) and to counter the progression of arthritis (U.S. Pat. No. 4,269,832) has likewise been described.

It has now been found, surprisingly, that 2,4,6-tris-tertiary-butylamino-1,3,5-triazine can be used for the treatment and prophylaxis of epileptic disorders and of anxiety states.

Thus the invention relates to 2,4,6-tris-tertiary-butylamino-1,3,5-triazine for the prophylaxis and treatment of epilepsy and anxiety states.

The invention also relates to medicaments which have a psychotropic action and which contain a compound of the formula I, and to the use of this compound for the preparation of a medicament. Finally, the invention also relates to a method for the prophylaxis and treatment of epileptic disorders and anxiety states.

The 2,4,6-tris-tertiary-butylamino-1,3,5-triazine is prepared as described in the literature, for example by baseor acid-catalyzed trimerization of tertiary-butylcyanamide (U.S. Pat. No. 2,691,021), by reaction of 2,4-bis(tert.-butylamino)-6-chloro-1,3,5-triazine with tertiary-butylamine (U.S. Pat. No. 3,591,693) or by reaction of cyanuric chloride with an excess of tertiary-butylamine (U.S. Pat. No. 4,296,832).

The triazine derivative 2,4,6-tris-tertiary-butylamino-1,3,5-triazine has pharmacological properties which indicate that it is a possible anticonvulsive and anxiolytic drug. The test designed by E. A. Swinyard has been used to examine the anticonvulsive action of the compound according to the invention in mice to prevent the convulsions induced by pentetrazole or by electric shock.

1. Antagonism to pentetrazole-induced convulsions (mice)

Method (E. A. SWINYARD, J. Pharmacol. Exp. Ther. 106, (1952), 319-330):

Groups of 10 male mice (Strain: NMRI; SPF-71, KF) weighing 18-22 g are used in this test. The test substances are suspended in a 1% strength suspension of ®Tylose (methylhydroxyethylcellulose) in water, and administered orally by gavage in a volume of 10 ml/kg body weight. The control group receives a corresponding volume of Tylose suspension containing no test substance. Pentetrazole (Cardiazol (®)) is injected subcutaneously in aqueous solution in a dose of 125 mg/kg body weight 1 hour after administration of the test substances. This dose induces tonic extensor spasms of the rear limbs in 90-100% of the control animals within the observation period of 60 minutes after the injection. The test substance is assessed as having a protective action if the number of animals with spasms is less than in the control group.

Where the test substance has a protective action a median effective dose ($ED_{50}$) is determined graphically (Litchfield and Wilcoxon) or by computation (probit analysis).

The $ED_{50}$ (50% inhibitory dose) after oral administration was determined to be 3.6 mg/kg test animal.

2. Antagonism to convulsions induced by electric shock (mouse)

Method (E. A. SWINYARD, In: Experimental Models of Epilepsy, Raven Press, New York, 1972, p. 433–458):

Groups of 6 male mice (Strain: NMRI, SPF-71, KF) weighing 18-22 g are used in this test. The test substances are suspended in a 1% strength suspension of Tylose (methylhydroxyethylcellulose) in water and administered orally by gavage in a volume of 10 ml/kg body weight. The control group receives a corresponding volume of Tylose suspension containing no test substance.

One hour after administration of the test substance an electric shock is administered to the animals via corneal electrodes (current strength 12-22 mA, duration 0.2 sec, 50 Hz) following previous determination, on a second control group, of the current strength which causes a tonic extensor spasm of the rear limbs in 100% of the animals.

The number of animals protected from an extensor spasm by the test substance serves as a measure of the anticonvulsive action in this test.

Where the test substance has a protective action a median effective dose (ED50) is determined graphically (Litchfield and Wilcoxon) or by computation (probit analysis).

The $ED_{50}$ (50% inhibitory dose) after oral administration was determined to be about 30 mg/kg test animal.

The anxiolytic action of the compound according to the invention has been tested in the lick-shock conflict test of J. R. Vogel (Psychopharmacologia 21 (1971) 1-7) and in the Geller-Seifter conflict test of I. Geller and J. Seifter (Psychopharmacologia 1 (1962), 482–492) on WISTAR rats.

3. Lick-shock conflict test:

Method:

Male Wistar rats of our own breed (SPF Hattersheim) weighing between 90 and 120 g are used. Drinking water is withdrawn from the animals for 48 hours before the test starts. The test entails the animals being placed in a plastic box (14×12×28 cm, w×d×h) which is equipped with a water bottle with a metal drinking tube and which also permits the number of contacts of the tongue of the animal with the drinking tube to be measured via an electronic circuit. The base of the box is made of metal rods through which a current can be passed by the electronic control system.

After the animals have been placed in the box they have 5 min to find the drinking tube and to lick it 50 times. Animals which have not found the drinking tube within this time are not used for the test. After these 50 lickings a current (direct current, 300 μA) is applied to the drinking tube and base rods for 5 sec periods with subsequent 5 sec intervals. This alternating sequence is continued for 5 min during which the number of contacts of the animal with the drinking tube during the period with irritating current and the period without irritating current are recorded on different electronic counters.

Groups of eight animals for each dose are treated orally by gavage with the test substance which is suspended in a 1% strength Tylose gel. The injection volume is 5 ml/kg body weight. The testing in the above-mentioned test apparatus is carried out 1 and 2 h after administration of the test substance. The number of contacts with the drinking tube in the irritating current period serve as the test variable. The mean number of contacts in this period in the control group is set at 100%, and an increase or decrease in the number of contacts by the animals treated with the test substance is expressed as a percentage of that in the control group.

In this test anxiolytics usually bring about a marked increase in the water intake (lickings) in the irritating current period compared with the untreated controls. If there is a linear or logarithmic relation between the dose and the action, an ED +100 (i.e. the dose which brings about an increase in the water intake of 100% compared with the control group) is calculated by regression analysis. If there is no linear dependence on the dose a minimal effective dose (MED) is determined, i.e. the lowest dose of the test substance which still brings about a statistically significant increase in the water intake compared with the control group ($p=0.05$, DUNNET test).

The minimal effective dose (MED) after oral administration is determined to be between 2 and 10 mg/kg test animal, and the percentage increase in the water intakes (lickings) is 90% (3 mg dose) or 125% (10 mg dose).

4. Geller-Seifter conflict test

Method:

Male Wistar rats of our own breed (SPF Hattersheim) weighing between 240 and 370 g are used and allocated to test groups each of 8 animals. 4 animals are placed in each plastic cage ($56 \times 38 \times 20$ cm) and maintained at about 80% of their normal body weight by weighing out the amounts of feed.

The animals are trained in a SKINNER box to press a button to receive a reward in the form of sweetened condensed milk. The box contains two buttons with microswitches, a loudspeaker, a domestic light, two signal lights above the buttons and a floor of metal rods. The training program was based on the paper of GELLER and SEIFTER (1962) as modified by DAVIDSON & COOK (Psychopharmacologia 15 (1969), 159–168): Each session comprises four 15-minute sections, all of which are composed of a 12-minute variable interval (VI) period and a 3-minute fixed ratio (FR) period. During the VI period, when the animals press the button they are rewarded with milk at an interval which is controlled by a random generator and lasts 10–110 sec with a mean of 60 sec. During the FR period, each time the animal presses the button it receives a reward but, in addition, at every 3rd pressing of the button a painful electrical stimulus is administered through the floor rods in order to set up a conflict situation. The current strength of the electrical stimulus is set individually for each animal (0.3–0.6 mA) so that the rate of pressing the button throughout the FR period is between 5 and 15.

The training takes place on 5 days a week, and tests with test substances are carried out once a week. Since the animals act as their own controls each test with the test substance is preceded by at least two preliminary tests without test substance. The test compound is suspended in a 1% strength Tylose gel and administered orally by gavage in a volume of 2 ml/kg 30 min before the test starts. Changes in the rate of pressing the button in the VI period are assessed as an effect on motor activity, and increases in the rate of pressing the button in the FR period are assessed as signs of an "anticonflict" or "anxiolytic action". It is usual to determine the minimal effective dose (MED) of the test substance, i.e. the lowest dose tested and found still to bring about a statistically significant change in the rate of pressing the button ($p=0.05$; WILCOXON matched pairs signed rank test).

The MED after oral administration is between 3 and 10 mg/kg test animal. The percentage increase in the accepted rewards is 158% (3 mg dose) or 235% (10 mg dose).

Since epileptic fits are frequently triggered by stress and anxiety situations the combination of antiepileptic and anxiolytic actions in the compound according to the invention is especially valuable.

By reason of the actions which have been indicated the compound of the formula I is suitable for the prophylaxis and treatment of epileptic disorders and anxiety states.

The medicaments according to the invention for the prophylaxis and treatment of epilepsy and anxiety states contain the triazine derivative of the formula I as active compound, where appropriate in combination with other active compounds.

The medicaments are prepared by methods known per se and familiar to the expert. The medicament is used in the form of tablets, coated tablets, capsules, suppositories, emulsions, suspensions or solutions with an effective amount of the said active compound either per se or, preferably, in combination with suitable pharmaceutical auxiliaries, the content of active compound being up to about 95%, preferably between 10 and 75%. The auxiliaries suitable for the desired medicament formulation are familiar to the expert on the basis of his expert knowledge. In addition to tableting auxiliaries, solvents, gel-forming agents, suppository bases and other vehicles for active compounds it is possible to use, for example, antioxidants, dispersants, emulsifiers, antifoam agents, flavorings, preservatives, solubilizers or colorants.

The active compound can be administered orally, parenterally, intravenously or rectally, with oral administration being preferred. For a form for oral use, the said active compound is mixed, where appropriate with further active compounds, with the additives suitable for this purpose, such as excipients, stabilizers or inert diluents, and converted by the customary methods into suitable presentations such as tablets, coated tablets, hard gelatin capsules and aqueous, alcoholic or oily suspensions or solutions. Examples of inert vehicles which can be used are gum arabic, magnesia, lactose, glucose or starch, in particular corn starch. Both dry and moist granules can be used for this preparation. Examples of suitable oily excipients or solvents are vegetable or animal oils, such as sunflower oil or fish liver oil.

For subcutaneous or intravenous administration, the active compound is converted into a solution, suspension or emulsion, if desired with the substances customary for this purpose, such as solubilizers, emulsifiers or other auxiliaries. Examples of suitable solvents are water, physiological saline solution or alcohols, for example, ethanol, propanol, or glycerol, as well as sugar solutions such as solutions of glucose or mannitol, or a mixture of the various solvents mentioned.

The dose which is to be administered each day will be selected to be appropriate for the desired effect. About 5 to 200 mg is administered, preferably orally, to a patient each day. When used as an antiepileptic the preferred dosage is 10 to 100 mg each day, the unit dose advantageously being 2.5 to 50 mg, preferably 2.5 to 25.0 mg. As an anxiolytic about 5 to 50 mg are administered each day in single doses between about 1.0 and 20 mg. Of course, it is also possible to use dosage units above or below this, and these must, if necessary, be divided or multiplied before administration.

EXAMPLE 1

Coated tablets

To prepare 1000 coated tablets 25 g of 2,4,6-tris-tertiary-butylamino-1,3,5-triazine, 50 g of corn starch, 35 g of lactose, 8.5 g of talc, 1 g of magnesium stearate and 0.5 g of colloidal silica are mixed and compressed to form tablet cores weighing 120 mg. The cores are coated with a coating mixture of 44.57 g of sucrose, 23.4 g of talc, 8 g of cellulose acetate phthalate, 2.24 g of castor oil and small amounts of gum arabic, titanium dioxide and wax, which is used so that the final weight of the coated tablets is 200 mg.

EXAMPLE 2

Tablets 1000 tablets are prepared from the following mixture: 50 g of 2,4,6-tris-tertiary-butylamino-1,3,5-triazine, 35 g of lactose, 50 g of corn starch, 13 g of talc and 2 g of magnesium stearate. The active compound and auxiliaries are mixed and, where appropriate after previous granulation, compressed to form tablets.

EXAMPLE 3

Capsules

To prepare 1000 hard gelatin capsules 10 g of 2,4,6-tris-tertiary-butylamino-1,3,5-triazine, 46 g of corn starch, 40 g of lactose and 4 g of colloidal silica are mixed. Nominal contents 100 mg/hard gelatin capsule.

EXAMPLE 4

Oral suspension

The oral suspension obtained from 50 g of sorbitol, 300 mg of sodium benzoate, 20 mg of saccharin, 100 mg of fruit flavoring and 1 g of 2,4,6-tris-tertiary-butylamino-1,3,5-triazine and distilled water ad 100 ml contains 10 mg of the active compound per ml.

We claim:

1. A medicament for the prophylaxis and treatment of epilepsy and anxiety states, which comprises an effective amount for said propylaxis and treatment of 2,4,6-tris-tertiary-butylamino-1,3,5-triazine and pharmacologically tolerated excipients.

2. A method for the treatment and prophylaxis of epilepsy and anxiety states, which comprises administering to a mammal in need of said treatment and prophylaxis an effective amount of 2,4,6-tris-tertiary-butylamino-1,3,5-triazine of the formula

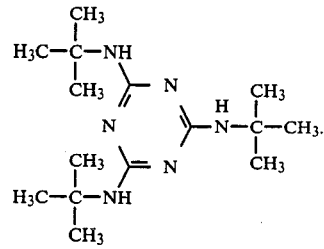

I

* * * * *